US011700999B2

(12) United States Patent
Goetz

(10) Patent No.: US 11,700,999 B2
(45) Date of Patent: Jul. 18, 2023

(54) AMBIENT BRIGHTNESS-BASED POWER SAVINGS FOR OPHTHALMIC DEVICE

(71) Applicant: Verily Life Sciences LLC, South San Francisco, CA (US)

(72) Inventor: Georges Goetz, Mountain View, CA (US)

(73) Assignee: Verily Life Sciences LLC

( * ) Notice: Subject to any disclaimer, the term of this patent is extended or adjusted under 35 U.S.C. 154(b) by 650 days.

(21) Appl. No.: 16/721,032

(22) Filed: Dec. 19, 2019

(65) Prior Publication Data

US 2020/0196852 A1 Jun. 25, 2020

Related U.S. Application Data

(60) Provisional application No. 62/782,808, filed on Dec. 20, 2018.

(51) Int. Cl.
| | | |
|---|---|---|
| A61B 3/00 | (2006.01) | |
| A61B 3/09 | (2006.01) | |
| G02C 11/00 | (2006.01) | |
| G02C 7/04 | (2006.01) | |
| A61F 2/16 | (2006.01) | |
| A61B 3/11 | (2006.01) | |

(52) U.S. Cl.
CPC .......... *A61B 3/0025* (2013.01); *A61B 3/0008* (2013.01); *A61B 3/09* (2013.01); *A61B 3/112* (2013.01); *A61F 2/1624* (2013.01); *G02C 7/041* (2013.01); *G02C 11/10* (2013.01); *A61F 2250/0001* (2013.01)

(58) Field of Classification Search
CPC ........ G02C 7/081; G02C 7/083; G02C 7/027; G02C 7/041; G02C 7/049; G02C 7/04; A61F 2/16; A61F 2/1618; A61F 2/1624; A61F 2250/0001; A61B 3/0008; A61B 3/0025; A61B 3/09; A61B 3/112
USPC ............................................ 351/210, 159.03
See application file for complete search history.

(56) References Cited

U.S. PATENT DOCUMENTS

| | | |
|---|---|---|
| 8,043,370 B2 | 10/2011 | Bretthauer et al. |
| 8,409,278 B2 | 4/2013 | Peyman et al. |
| 8,834,566 B1 | 9/2014 | Jones |
| 9,226,818 B2 | 1/2016 | Campin et al. |
| 9,241,669 B2 | 1/2016 | Pugh et al. |
| 9,259,309 B2 | 2/2016 | Fehr et al. |
| 9,323,073 B2 | 4/2016 | Pugh et al. |
| 2009/0015785 A1 | 1/2009 | Blum et al. |
| 2012/0140167 A1 | 6/2012 | Blum |
| 2013/0242256 A1* | 9/2013 | Fehr .......................... A61B 3/09 351/205 |

(Continued)

*Primary Examiner* — Zachary W Wilkes
(74) *Attorney, Agent, or Firm* — Christensen O'Connor Johnson Kindness PLLC

(57) ABSTRACT

Accommodating ophthalmic devices including an ambient light sensor and an accommodation sensor and related methods of use are described. In an example, the accommodation sensor is configured to measure a biological accommodation signal of an eye on or in which the accommodating ophthalmic device is mounted. In an embodiment, the accommodating ophthalmic device is configured to measure the biological accommodation signals based on ambient light, such as based on an intensity or amount of ambient light, incident on the accommodating ophthalmic device. Such ambient light may be measured with the ambient light sensor.

12 Claims, 6 Drawing Sheets

(56) References Cited

U.S. PATENT DOCUMENTS

| | | | |
|---|---|---|---|
| 2014/0022505 A1* | 1/2014 | Pugh | G02C 11/10 |
| | | | 351/159.03 |
| 2014/0240658 A1* | 8/2014 | Pugh | G02C 7/04 |
| | | | 623/6.22 |
| 2014/0240665 A1* | 8/2014 | Pugh | A61B 3/112 |
| | | | 351/205 |
| 2015/0088253 A1 | 3/2015 | Doll et al. | |
| 2015/0173893 A1 | 6/2015 | Portney | |
| 2015/0182116 A1* | 7/2015 | Pletcher | A61B 5/0015 |
| | | | 600/345 |
| 2015/0362756 A1* | 12/2015 | Wiser | G02C 7/049 |
| | | | 351/210 |
| 2016/0324628 A1* | 11/2016 | Gupta | A61F 2/1659 |
| 2017/0079771 A1 | 3/2017 | Roholt et al. | |
| 2017/0354326 A1* | 12/2017 | Pugh | G02C 7/083 |

\* cited by examiner

AMBIENT BRIGHTNESS-BASED POWER SAVINGS FOR OPHTHALMIC DEVICE

CROSS-REFERENCE TO RELATED APPLICATION

This application claims the benefit of U.S. Provisional Application No. 62/782,808, filed Dec. 20, 2018, which is hereby incorporated by reference in its entirety.

TECHNICAL FIELD

This disclosure relates generally to ophthalmic devices and, in particular but not exclusively, relates to accommodating ophthalmic devices.

BACKGROUND INFORMATION

Cataracts and presbyopia may be treated with implantable lenses that provide accommodation. Cataract treatment generally includes implantation of a replacement lens. Such lenses, which may also be referred to as intraocular lenses, may provide static accommodation, dynamic accommodation, or a combination thereof. Various techniques may be available to provide dynamic accommodation, such as mechanical or electrical controlled accommodation. The accommodation may be provided by actuation of a dynamic optical component that provides multiple levels of optical power. The change in optical power may provide different focal distances to the user via the intraocular lens. The amount of actuation, however, may depend on the technique used, e.g., mechanical or electrical. For successful treatment of presbyopia, an implanted lens may include a dynamic optical component. Presbyopia may also be treated with contact lenses that provide accommodation.

The amount and precision and/or accuracy of accommodation may depend on the technique(s) used to provide accommodation and to sense a target optical power of the eye. Generally, more precise and/or accurate sensing of a target optical power of an eye uses more electrical power. Use of such relatively high levels of electrical power may present challenges to accommodating ophthalmic devices and power sources disposed therein.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Figure 1A:
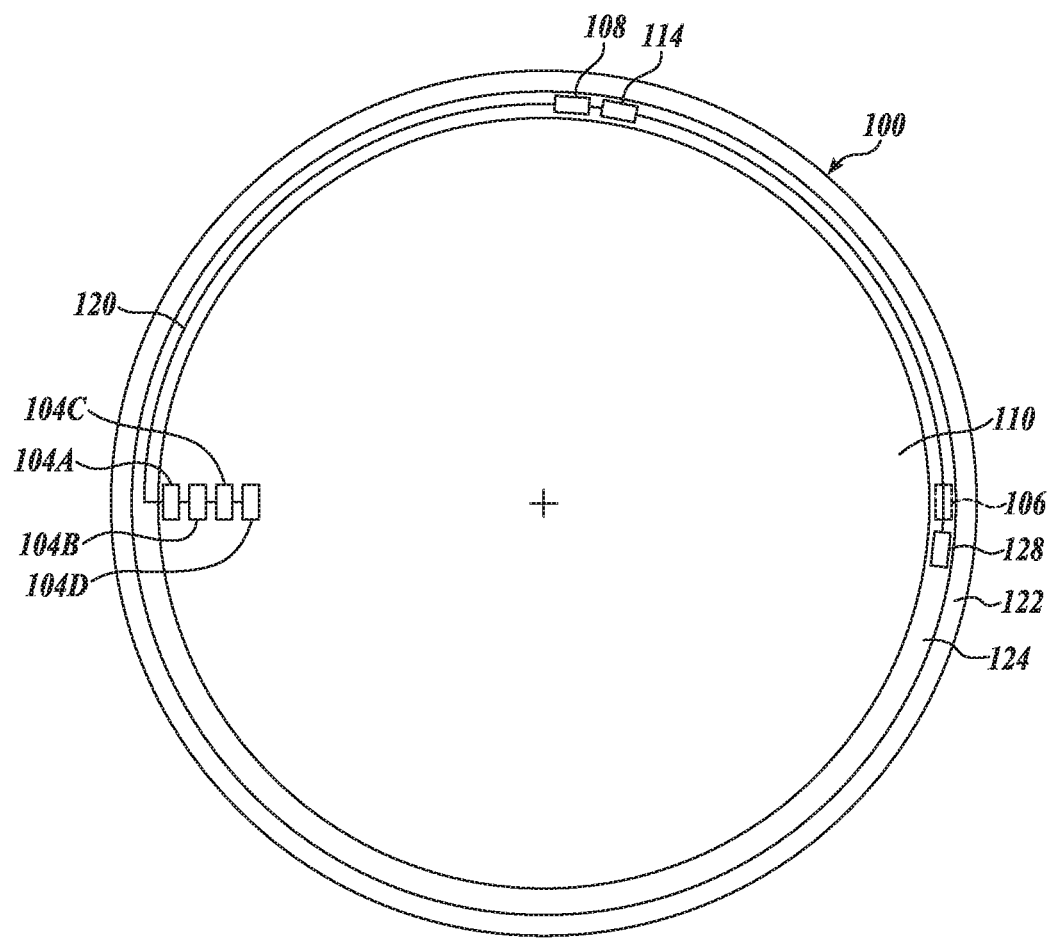
FIG. 1A is a top-down plan view of an ophthalmic device, in accordance with an embodiment of the disclosure.

Embodiments of an ophthalmic device for and method for manipulating measuring a biological accommodation signal based on ambient light incident on the ophthalmic device are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Accommodating ophthalmic devices are typically configured to change an optical power of the accommodating ophthalmic device based on a target optical power of an eye on or in which the accommodating ophthalmic device is mounted. Generally, accommodating ophthalmic devices, such as smart contact lenses or accommodating intraocular lenses, have constraints on how much electrical power the accommodating ophthalmic device can use due to, for example, power constraints on power sources in the ophthalmic device. Such constraints may limit what types of and how accommodation sensors may be used in the accommodating ophthalmic devices and processing power available to interpret data generated by accommodation sensors. Further, accommodation sensors may use more power when used in a manner to obtain a higher-precision and/or higher-accuracy measurement of a target optical power of the eye. In this regard, many accommodation sensors have trade-offs with respect to power consumption and performance. For example, averaging multiple measurements of the same signal is a straightforward way to improve the precision/accuracy of an accommodation measurement. Such a measurement typically includes repeatedly measuring a target optical power. Improvement in signal-to-noise ratio then scales as the square root of the number of measurement repeats, while the power footprint of the sensor scales linearly with the number of repeats.

Under bright illumination conditions, the pupil of the human eye generally constricts, which results in an increase in the depth of field of the image projected onto the back of the eye, and a decrease in aberrations introduced by larger diameter optics. Conversely, in low-light conditions, the pupil can significantly increase in diameter, which results in a smaller depth of field in the retinal image and makes the eye much more sensitive to defocus. In other words, under bright illumination conditions, the human eye is intrinsically more robust to defocus than under low-light illumination conditions.

Because the sensitivity to defocus of the eye is decreased by the closure of the pupil in bright-illumination conditions, more efficient designs are possible by accepting lower accuracy of accommodation, which won't be very noticeable to the user, to measure a target optical power of the eye with the same precision and/or accuracy in both bright- and low-light-illumination conditions. Accordingly, the present disclosure provides accommodating ophthalmic devices configured, for example, to manipulate the measuring of the biological accommodation signals based upon the ambient light conditions. In an embodiment, the ophthalmic devices are configured to degrade performance of an accommodation sensor as the system detects increases in brightness of illumination conditions, as the eye is naturally less sensitive to defocus and compensates for the degraded performance. Correspondingly, in an embodiment, the ophthalmic devices of the present disclosure are configured to improve performance of an accommodation sensor as the system detects a decrease in brightness of illumination conditions.

Figure 1B:
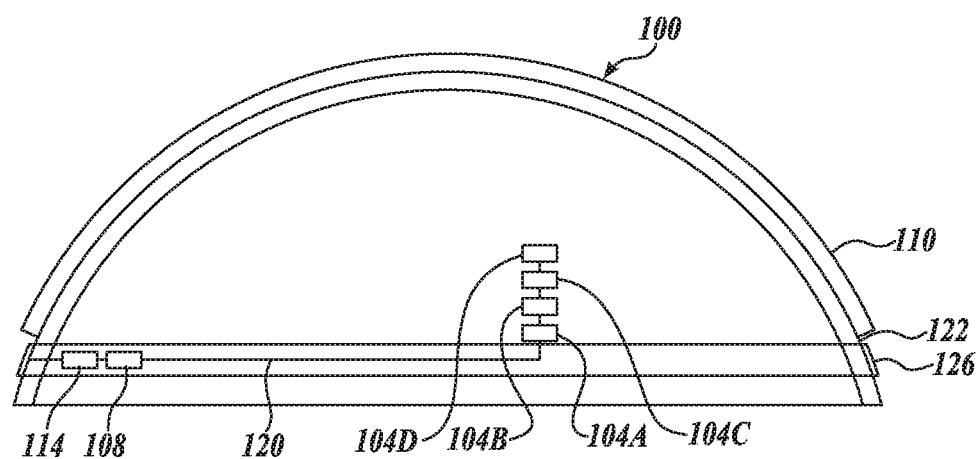
FIG. 1B is a view in cross-section of the ophthalmic device of FIG. 1A, in accordance with an embodiment of the disclosure.
Figure 1C:
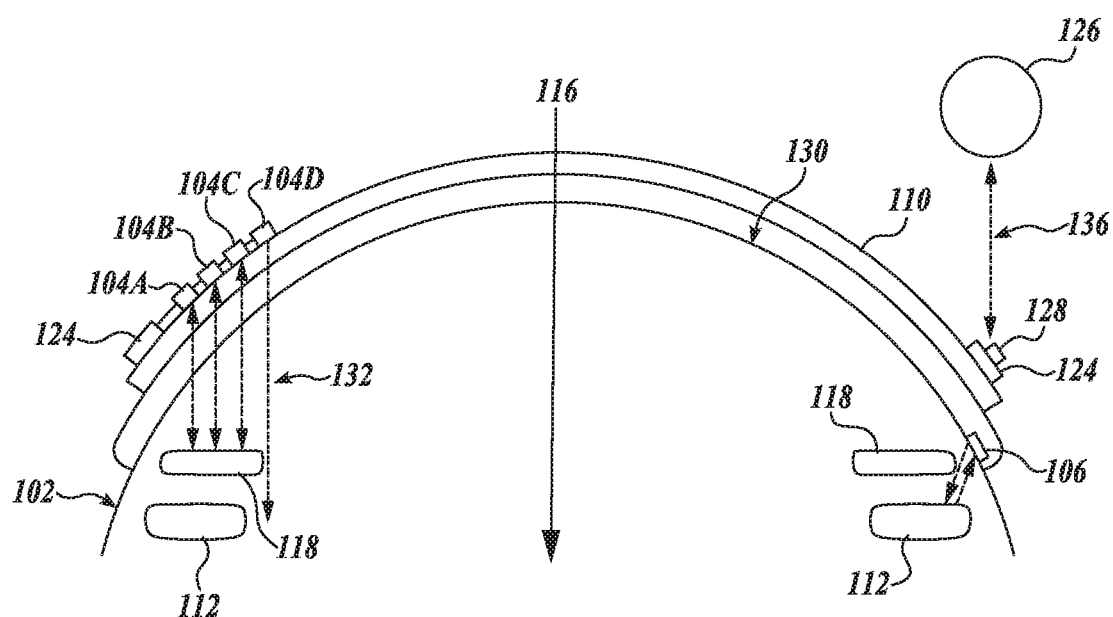
FIG. 1C another view in cross-section of the ophthalmic device of FIG. 1A, shown mounted on an eye, in accordance with an embodiment of the disclosure.

FIGS. 1A-1C illustrate an ophthalmic device 100 shaped to be mounted on an eye, in accordance with an embodiment of the disclosure. FIG. 1A is a top-down plan view of an ophthalmic device 100. FIG. 1B is a view in cross-section of the ophthalmic device 100. FIG. 1C another view in cross-section of the ophthalmic device 100, shown mounted to an eye 102, in accordance with an embodiment of the disclosure.

As shown, ophthalmic device 100 includes ambient light sensors 104A-104D, an accommodation sensor 106, and a controller 108. In the illustrated embodiment, ophthalmic device 100 is shaped to be mounted on an eye 102, such as on a corneal surface 130 of the eye 102, as a contact lens. See FIG. 1C. In the illustrated embodiment, ambient light sensors 104A-104D are disposed on lens body 120 and controller 108 and accommodation sensor 106 are disposed on substrate 124 disposed on lens body 122. Ambient light sensors 104A-104D and accommodation sensor 106 are operatively coupled to controller 108 through conductive traces 120.

Controller 108 includes logic that, when executed by the controller 108, causes the ophthalmic device 100 to perform operations. Such operations can include measuring, with the ambient light sensors 104A-104D, ambient light incident upon the ophthalmic device 100; and generating an ambient light signal based on the ambient light incident upon the ophthalmic device 100. As discussed further herein, such an ambient light signal can include a signal based on a level or amount of ambient light incident upon the ophthalmic device 100. As discussed further herein, such an ambient light signal can be based on a diameter of a pupil 116 of the eye 102. In this regard, the ambient light sensors 104A-104D are configured to measure ambient light incident upon the eye 102 when the ophthalmic device 100 is mounted on or in the eye 102.

Such operations can further include measuring with the accommodation sensor 106 the biological accommodation signals; and generating an accommodation control signal based upon the measuring of the biological accommodation signals.

The operations can further include manipulating the measuring of the biological accommodation signals based upon the ambient light signal. Such manipulation may include changing an aspect of measuring the biological accommodation signals to change an accuracy and/or precision of a target optical power of an eye 102 based on ambient light incident upon the ophthalmic device 100. As discussed further herein, under bright illumination conditions, the human eye is less sensitive to defocus than under low-light illumination conditions. In this regard, measuring may be tailored to ambient light conditions and attendant susceptibility of the eye to defocus.

Further, in an embodiment, the operations include generating accommodation control signal more closely based on the target optical power of the eye 102 when a level of the ambient light signal is below a predetermined level than when the level of ambient light signal is at or above the predetermined level. In an embodiment, the predetermined level is one of a plurality of predetermined levels below which the operations include generating progressively more precise/accurate accommodation control signal as a level of ambient light incident upon the ophthalmic device 100 decreases. In one embodiment, the operations include continuously increasing a precision/accuracy of accommodation control signal as the level of ambient light signals decreases.

As shown, the ophthalmic device 100 further includes an accommodation actuator 110 configured to change an optical power of the ophthalmic device 100 operatively coupled to the controller 108. In an embodiment, the controller 108 further includes logic that, when executed by the controller 108, causes the ophthalmic device 100 to perform operations including driving the accommodation actuator 110 based at least in part on the accommodation control signal to change an optical power of the ophthalmic device 100. In this regard, the ophthalmic device 100 is configured to adjust an optical power of the ophthalmic device 100 based upon the biological accommodation signals, as measured.

Manipulating the measuring of the biological accommodation signals can include a number of manipulations to such measurements that are proportional to or otherwise based upon ambient light incident upon the ophthalmic device 100. In an embodiment, manipulating includes manipulating measuring the biological accommodation signals to improve an accuracy and/or a precision of the biological accommodation signal in low-light conditions, such as below the predetermined level. In that regard, as the measuring biological accommodation signals is manipulated and accommodation control signal is generated that, for example, more accurately and/or precisely reflect a target optical power of an eye 102, the accommodation actuator 110 is configured to change an optical power based on such more accurate and/or precise accommodation control signal. Accordingly, in an embodiment, an optical power of the eye 102 on or in which the ophthalmic device 100 is mounted is closer to the target optical power when the level of the ambient light signal is below the predetermined level than when the level of the ambient light signal is at or above the predetermined level. In that regard, the ophthalmic device 100 is configured to compensate for the inherent susceptibility of an eye to defocus in low-light conditions, such as those below the predetermined level.

Likewise, in an embodiment, manipulating includes manipulating measuring the biological accommodation signals to reduce a power consumption rate, for example, at the expense of an accuracy and/or precision of the biological accommodation signals, such as under bright-light illumination at or above the predetermined level.

In an embodiment, manipulating the measuring of the biological accommodation signals includes changing a number of biological accommodation signal measurements used to generate the accommodation controls signal. By using fewer biological accommodation signal measurements, such as under bright-light illumination conditions, fewer computations, such as by the controller 108, are used to generate the accommodation control signal, and accordingly, less power is used by the ophthalmic device 100. Correspondingly, by using more biological accommodation signal measurements, such as under low-light illumination conditions and where ambient light signals are under a predetermined level, accommodation control signal more accurately and/or precisely reflect a target optical power of the eye.

In an embodiment, manipulating the measuring of the biological accommodation signals includes manipulating a size of an averaging window of biological accommodation signal measurements. By increasing the size of an averaging window of biological accommodation signal measurements, more computation power may be used than compared to a smaller averaging window. However, an average of the biological accommodation signal taken over a larger averaging window is generally more precise and/or accurate than a smaller averaging window. In one embodiment, manipulating the averaging window of biological accommodation signal measurements includes increasing a size of the averaging window when a level of the ambient light signal is below the predetermined level. In one embodiment, manipulating the averaging window of biological accommodation signal measurements includes decreasing a size of the averaging window when a level of the ambient light signal is at or above the predetermined level, thereby generally using less power to generate accommodation control signal than if the averaging window were larger.

In an embodiment, manipulating the measuring of the biological accommodation signals includes manipulating a biological accommodation signal measurement frequency. By increasing a frequency of biological accommodation signal measurements, more power may be used as more biological accommodation signal measurements are made in a given period of time, than compared with lower biological accommodation signal frequency. However, accommodation control signal based on biological accommodation signal measurements obtained at a higher frequency may be more accurate and/or precise in representing a target optical power of the eye. In one embodiment, manipulating a biological accommodation signal measurement frequency includes increasing a biological accommodation signal measurement frequency, such as when an ambient light signal level is below a predetermined level, to compensate for the eye's natural susceptibility to defocus at such relatively low ambient brightness. In one embodiment, manipulating a biological accommodation signal measurement frequency includes decreasing a biological accommodation signal measurement frequency, such as when an ambient light signal level is at or above a predetermined level. In this regard, sensing performance is degraded to use less power when the eye is less susceptible to defocus.

In an embodiment, manipulating the measuring of the biological accommodation signals includes manipulating a biological accommodation signal bit and/or sampling rate, such as during digitizing the biological accommodation signal. By increasing a bit and/or sampling rate of the biological accommodation signal the ophthalmic device 100 may consume more power. Further, by increasing a bit and/or sampling rate of the biological accommodation signal, the ophthalmic device 100 may generate more precise and/or accurate accommodation control signal based on the biological accommodation signals generated at the increased bit and/or sampling. Accordingly, in one embodiment, manipulating the measuring of the biological accommodation signals includes manipulating a biological accommodation signal bit and/or sampling rate when an ambient light signal is below a predetermined level, such as in low-light conditions. In one embodiment, manipulating the measuring of the biological accommodation signals includes manipulating a biological accommodation signal bit and/or sampling rate by decreasing a bit and/or sampling rate when an ambient light signal is at or above the predetermined level, such as in bright-light conditions.

Ophthalmic device 100 includes ambient light sensors 104A-104D for measuring ambient light incident upon ophthalmic device 100. As discussed further herein, in an embodiment, ambient light sensors 104A-104D may be configured to generate ambient light signals, which may be used to manipulate measuring biological accommodation signals. Ambient light sensors 104A-104D are positioned to measure ambient light incident upon the ophthalmic device 100. In the illustrated embodiment, ambient light sensors 104A-104D are shaped and positioned to measure a diameter of a pupil 116 when the ophthalmic device 100 is mounted on or in the eye 102. In this regard, ambient light sensors 104A-104D are shaped and positioned to measure ambient light incident upon the ophthalmic device 100 indirectly by measuring a diameter of the pupil 116, which varies with ambient light incident upon the eye 102. In an embodiment, ambient light sensors 104A-104D are configured to measure the diameter of the pupil 116 when the ophthalmic device 100 is mounted on or in the eye 102 in a way that compensates for factors other than incident light that will affect a diameter of the pupil 116. In this regard, the ophthalmic device 100 is configured to measure pupil size as a proxy for ambient light incident upon the ophthalmic device 100 when mounted on or in the eye 102.

As shown in FIG. 1C, ambient light sensors 104A-104D emit ambient light interrogation signal 132, such as an optical or ultrasound signal. In the illustrated embodiment, a portion of the ambient light interrogation signal 132 impinges upon an iris 118 of the eye 102 when the ophthalmic device 100 is mounted on or in the eye 102, whereas another portion of the ambient light interrogation signal 132 does not impinge upon the iris 118, but rather passes through the pupil 116. In this regard, the ambient light sensors 104A-104D are configured to measure a diameter of the pupil 116 based on, for example, the number and position of the ambient light sensors 104A-104D that emit ambient light interrogation signal 132 and receive reflected/scattered ambient light interrogation signal 132. As the level of ambient light decreases, the size of the pupil 116 generally increases and fewer ambient light sensors 104A-104D receive reflected/scattered ambient light interrogation signal 132. In an embodiment, a predetermined level of the ambient light signal is based upon a number of ambient light sensors 104A-104D that receive reflected/scattered ambient light interrogation signal 132. For example, the predetermined level of ambient light signal may include, for example, when three out of four ambient light sensors 104A-104D receive reflected/scattered ambient light interrogation signal 132 reflected/scattered off of an iris 118. In the illustrated embodiment, ambient light sensors 104A-104C receive reflected/scattered ambient light interrogation signal 132, whereas ambient light interrogation signal 132 emitted by ambient light sensor 104D passes through the pupil 116 and does not impinge upon the iris 118.

While multiple ambient light sensors 104A-104D are illustrated, it will be understood that the ophthalmic device 100 may include a single ambient light sensor, such as an ambient light sensor configured to generate an ambient light signal proportional to an amount or an intensity of ambient light incident upon the ophthalmic device 100. In an embodiment, the ophthalmic device 100 includes a plurality of ambient light sensors, wherein ambient light sensors of the plurality of ambient light sensors are configured to provide different responses and generate different signals based on varying amounts of received ambient light. In this regard, the plurality of light sensors is configured to generate ambient light signals proportional to and based on received ambient light over a wide range of ambient light intensities.

Ophthalmic device 100 further includes an accommodation sensor 106 configured to measure biological accommodation signals indicative of a target optical power of the eye 102. In an embodiment, the accommodation sensor 106 is an electromyography sensor 106 configured to generate the accommodation control signal based at least in part upon electrical activity of ciliary muscles 112 of the eye 102. Such electrical activity of the ciliary muscles 112 may indicate a target optical power of the eye 102. Accordingly, an accommodation actuator 110 may be driven based upon accommodation control signal based upon such electrical activity to provide an optical power mimicking the target optical power of the eye 102.

In the illustrated embodiment, ophthalmic device 100 includes an electromyography sensor 106 and an amplifier 114 configured to amplify the level of the accommodation control signal. Such amplification may be suitable to increase a signal-to-noise ratio of the accommodation control signal. In one embodiment, the controller 108 further includes logic that when executed by the controller 108 causes the ophthalmic device 100 to perform operations including: increasing a gain of the amplifier 114 when the level of the ambient light signal is below the predetermined level. By increasing a gain of the amplifier 114, the biological accommodation signals may be measured more accurately and/or more precisely compared to with a lower amplifier 114 gain.

As discussed further herein, the controller 108 may include logic that when executed by the controller causes the ophthalmic device 100 to manipulate the measuring of the biological accommodation signals based upon the ambient light signal. In an embodiment, manipulating the measuring of the biological accommodation signals includes manipulating a gain of the amplifier 114. In an embodiment, manipulating the gain of the amplifier 114 includes increasing a gain of the amplifier 114 when the level of the ambient light signal is below a predetermined level, such as under low-light conditions. By increasing the gain of the amplifier 114, the ophthalmic device 100 may generate more accurate and/or precise accommodation control signal based on the amplified biological accommodation signals than at a lower amplifier 114 gain. In an embodiment, manipulating the gain of the amplifier 114 includes decreasing a gain of the amplifier 114 when the level of the ambient light signal is at or above a predetermined level, such as under bright-light conditions. By decreasing the gain of the amplifier 114, the ophthalmic device 100 may use less power in generating the accommodation control signal than at a higher amplifier 114 gain.

In the illustrated embodiment, ophthalmic device 100 further includes a second accommodation sensor 128 configured to measure the biological accommodation signals of the eye 102 and generate second accommodation control signal based on the biological accommodation signals. The second accommodation sensor 128 may be operatively coupled to the controller 108, which includes logic that when executed by the controller 108 causes the ophthalmic device 100 to perform operations including measuring with the second accommodation sensor 128 the biological accommodation signals. In this regard, the ophthalmic device 100 is configured to measure two or more biological accommodation signals and/or measure a single biological accommodation signal with two accommodation sensors.

In an embodiment, the controller 108 includes logic that when executed by the controller 108 causes the ophthalmic device 100 to perform operations including measuring, with the second accommodation sensor 128, the biological accommodation signals when the level of the ambient light signal is below the predetermined level. In this regard, the second accommodation sensor 128 may be activated under low-light conditions in which increased accuracy and/or precision of the second accommodation sensor 128 are suitable to compensate for the inherent sensitivity of the eye 102 to defocus under such conditions.

In an embodiment, the second accommodation sensor 128 is configured to more accurately and/or precisely measure the biological accommodation signals than the first accommodation sensor 106. For example, the second accommodation sensor 128 may be a time-of-flight accommodation sensor 128 configured to emit a time-of-flight interrogation signal 136 and positioned to emit the time-of-flight interrogation signal 136 in a direction of gaze of the ophthalmic device 100, whereas the first accommodation sensor 106 is an optical sensor configured to measure position and/or displacement of ciliary muscles of the eye. In that regard, time-of-flight interrogation signal 136 may impinge upon and be reflected and/or scattered by an object 126 in the direction of gaze of a user. The controller 108 may include logic that when executed by the controller 108 causes the ophthalmic device 100 to calculate a time between when the time-of-flight interrogation signal 136 was emitted from the second accommodation sensor 128 and when the reflected/scattered time-of-flight interrogation signal 136 was received by the second accommodation sensor 128. In this regard, the ophthalmic device 100 is configured to further calculate a distance between the ophthalmic device 100 and the object 126 in the direction of gaze based upon a speed of the time-of-flight interrogation signal 136. Such a distance may be indicative of a target optical power of the eye 102 and may be used to generate accommodation control signal based upon a target optical power of the eye 102.

In an embodiment, the second accommodation sensor 128 has a power-consumption rate greater than a power-consumption rate of the first accommodation sensor 106. For example, time-of-flight accommodation sensors may have relatively high power consumption rates compared to other types of accommodation sensors due in part to the number of time-of-flight interrogation signal 136 emitted and the processing power used to interpret reflected/scattered time-of-flight interrogation signal 136. Accordingly, in an embodiment, such a second accommodation sensor 128 may be activated when an ambient light signal level is below a predetermined level in order to conserve power under bright-light conditions.

As shown, ophthalmic device 100 further includes an accommodation actuator 110 operatively coupled to controller 108 and configured to change an optical power of the ophthalmic device 100. Controller 108 may include logic that when executed by the controller 108 causes the ophthalmic device 100 to perform operations including driving the accommodation actuator 110 based at least in part on the accommodation control signal to change an optical power of the ophthalmic device 100. In this regard, an optical power of the eye 102 on or in which the ophthalmic device 100 is mounted may be closer to the target optical power when the level of the ambient light signal is below the predetermined level than when the level of the ambient light signal is at or above the predetermined level due to the increased accuracy and/or precision of the measurement of the biological accommodation signals under such ambient light signals.

Figure 2A:
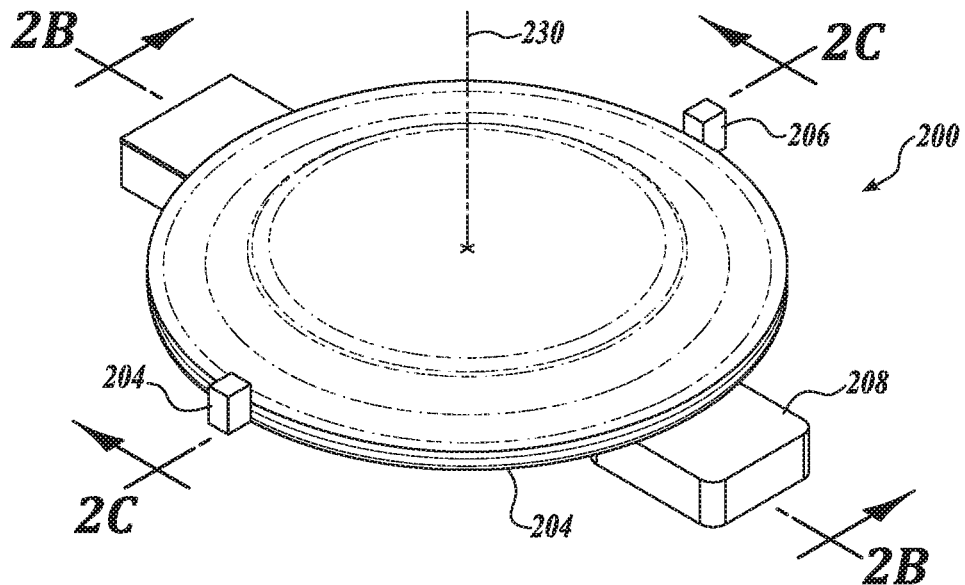
FIG. 2A is a perspective view of an ophthalmic device, in accordance with an embodiment of the disclosure.
Figure 2B:
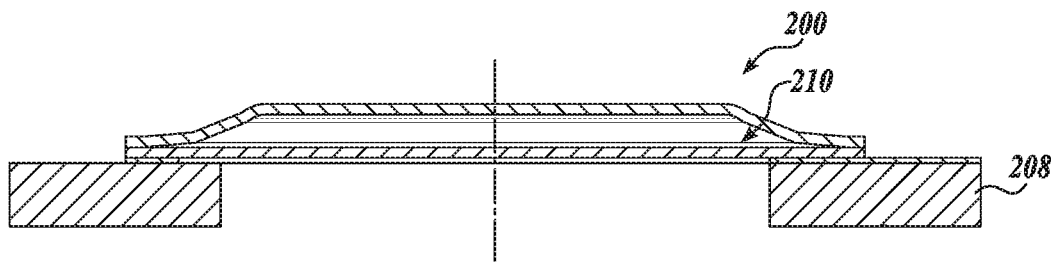
FIG. 2B is a view in cross-section of the ophthalmic device of FIG. 2A, in accordance with an embodiment of the disclosure.
Figure 2C:
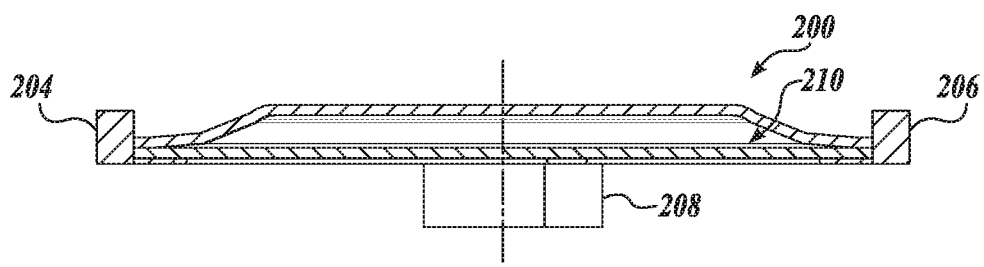
FIG. 2C is another view in cross-section of the ophthalmic device of FIG. 2A, in accordance with an embodiment of the disclosure.

In an embodiment, the ophthalmic devices of the present disclosure are shaped to be mounted or otherwise implanted in an eye. In that regard, attention is directed to FIGS. 2A-2D, in which an ophthalmic device 200, in accordance with an embodiment of the disclosure, is illustrated. FIG. 2A is a perspective view of ophthalmic device 200. FIG. 2B is a view in cross-section of the ophthalmic device 200. FIG. 2C is another view in cross-section of the ophthalmic device 200.

Ophthalmic device 200 is shown to include an ambient light sensor 204 positioned to measure ambient light incident upon the ophthalmic device 200; an accommodation sensor 206 configured to measure biological accommodation signals based upon a target optical power of the eye; an accommodation actuator 210 configured to change an optical power of the ophthalmic device 200, and a controller 208 operatively coupled to the ambient light sensor 204 and the accommodation sensor 206.

Controller 208 includes logic that, when executed by the controller 208, causes the ophthalmic device 200 to perform certain operations. Controller 208 is operatively coupled to the ambient light sensor 204, accommodation sensor 206, and accommodation actuator 210 and thus configured to receive and transmit signals to and from the ambient light sensor 204, accommodation sensor 206, and accommodation actuator 210.

In an embodiment, the controller 208 includes logic that when executed by the controller 208 causes the ophthalmic device 200 to perform operations including: measuring, with the ambient light sensor 204, ambient light incident upon the ophthalmic device 200; generating an ambient light signal based on a brightness of the ambient light incident upon the ophthalmic device 200; measuring, with the accommodation sensor 206, the biological accommodation signals; and manipulating the measuring of the biological accommodation signals based upon the ambient light signal; and generating an accommodation control signal based upon the measuring of the biological accommodation signals.

Figure 2D:
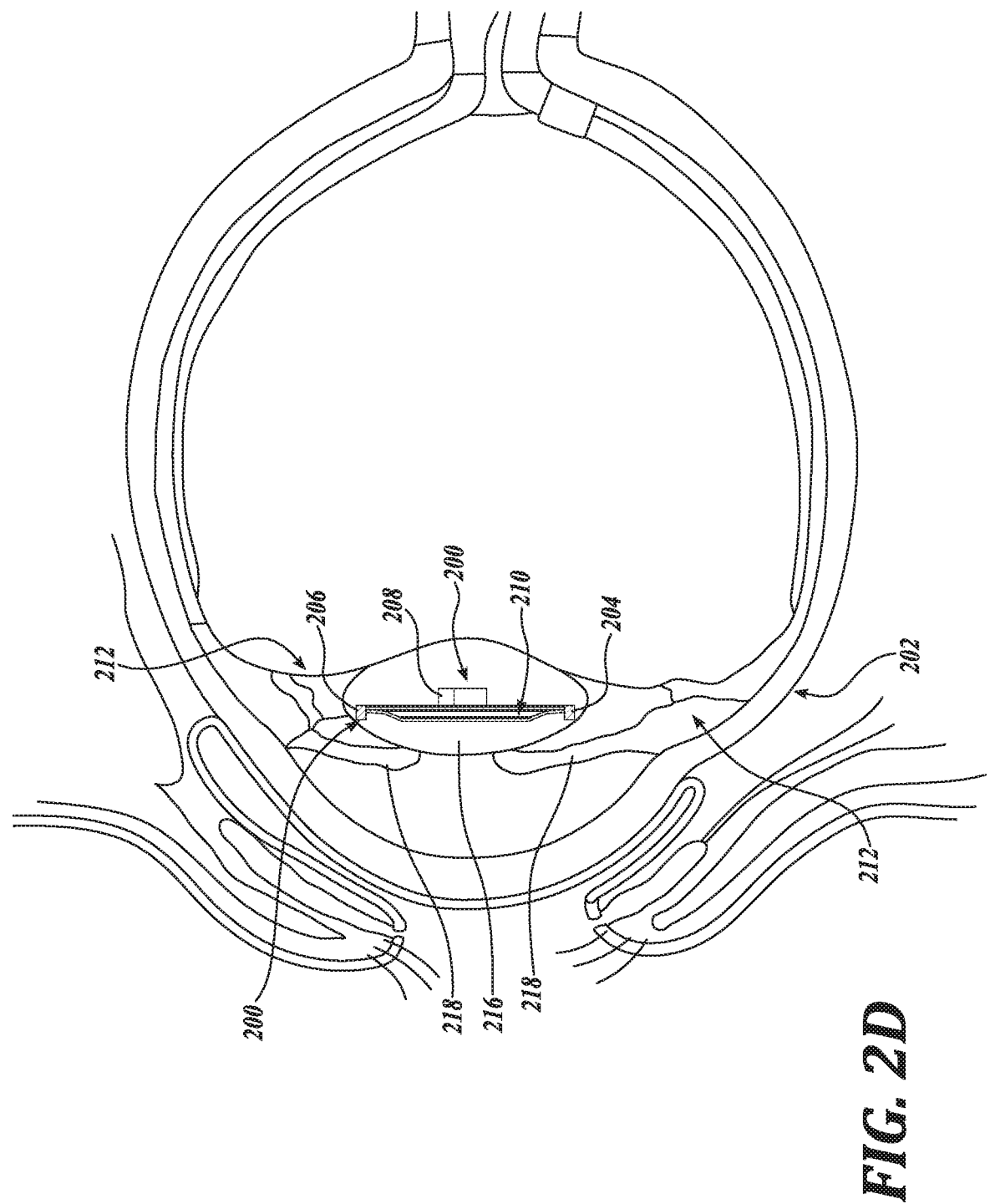
FIG. 2D is another view in cross-section of the ophthalmic device of FIG. 2A shown mounted in an eye, in accordance with an embodiment of the disclosure.

FIG. 2D is another view in cross-section of the ophthalmic device 200 of FIG. 2A shown mounted in an eye 202, in accordance with an embodiment of the disclosure. In the illustrated embodiment, ophthalmic device 200 is shown implanted in a lens 238 of an eye 202. It will be understood, however, that the ophthalmic devices of the present disclosure can be configured to be implanted in various portions of the eye 202 depending upon, for example, the size of the ophthalmic devices, the nature of the accommodation actuator 210 disposed therein, and the biological accommodation signals such ophthalmic devices are configured to measure. In the illustrated embodiment, the ambient light sensor 204 is a light-sensitive element 204 positioned to face away from a body of a user when the ophthalmic device 200 is mounted on or in the eye 202 and to measure the light incident upon the ophthalmic device 200. In this regard, the ambient light sensor 204 is configured to measure ambient light incident upon the ophthalmic device 200 directly. The light-sensitive element 204 can be any light sensitive element 204 configured to generate ambient light signal based upon the ambient light incident upon the ophthalmic device 200. In an embodiment, the light-sensitive element 204 is selected from the group consisting of a photovoltaic device, a photodiode, and a photo-transistor. In an embodiment, the light-sensitive element 204 is configured to generate an ambient light signal that is proportional to an intensity or an amount of ambient light incident upon the ophthalmic device 200.

As above, ophthalmic device 200 includes accommodation sensor 206 for measuring biological accommodation signals of the eye 202. In an embodiment, the accommodation sensor 206 is configured to generate an accommodation control signal based upon the biological accommodation signals. In an embodiment, generating the accommodation control signal includes generating accommodation control signal more closely based on the target optical power of the eye 202 when a level of the ambient light signal is below a predetermined level than when the level of ambient light signal is at or above the predetermined level. In that regard, an optical power of the eye 202 on or in which the ophthalmic device 200 is mounted may be closer to the target optical power when the level of the ambient light signal is below the predetermined level than when the level of the ambient light signal is below the predetermined level due to the increased accuracy and/or precision with which the biological accommodation signals are measured.

In an embodiment, accommodation sensor 206 is configured to measure a position and/or displacement of ciliary muscles 212 of the eye 202. Ciliary muscles 212 of the eye 202 control accommodation and, accordingly, position and/or displacement of the ciliary muscles 212 can be indicative of a target optical power of the eye 202. In the illustrated embodiment, the accommodation sensor 206 emits an accommodation interrogation signal that impinges on and is reflected and/or scattered by the ciliary muscles 212. As described further herein, the ophthalmic device 200 is configured to generate accommodation control signal based upon the measured biological accommodation control signal. As also described further herein, measuring with the accommodation sensor 206 may be manipulated based upon ambient light signal generated by the ambient light sensor(s).

Figure 4:
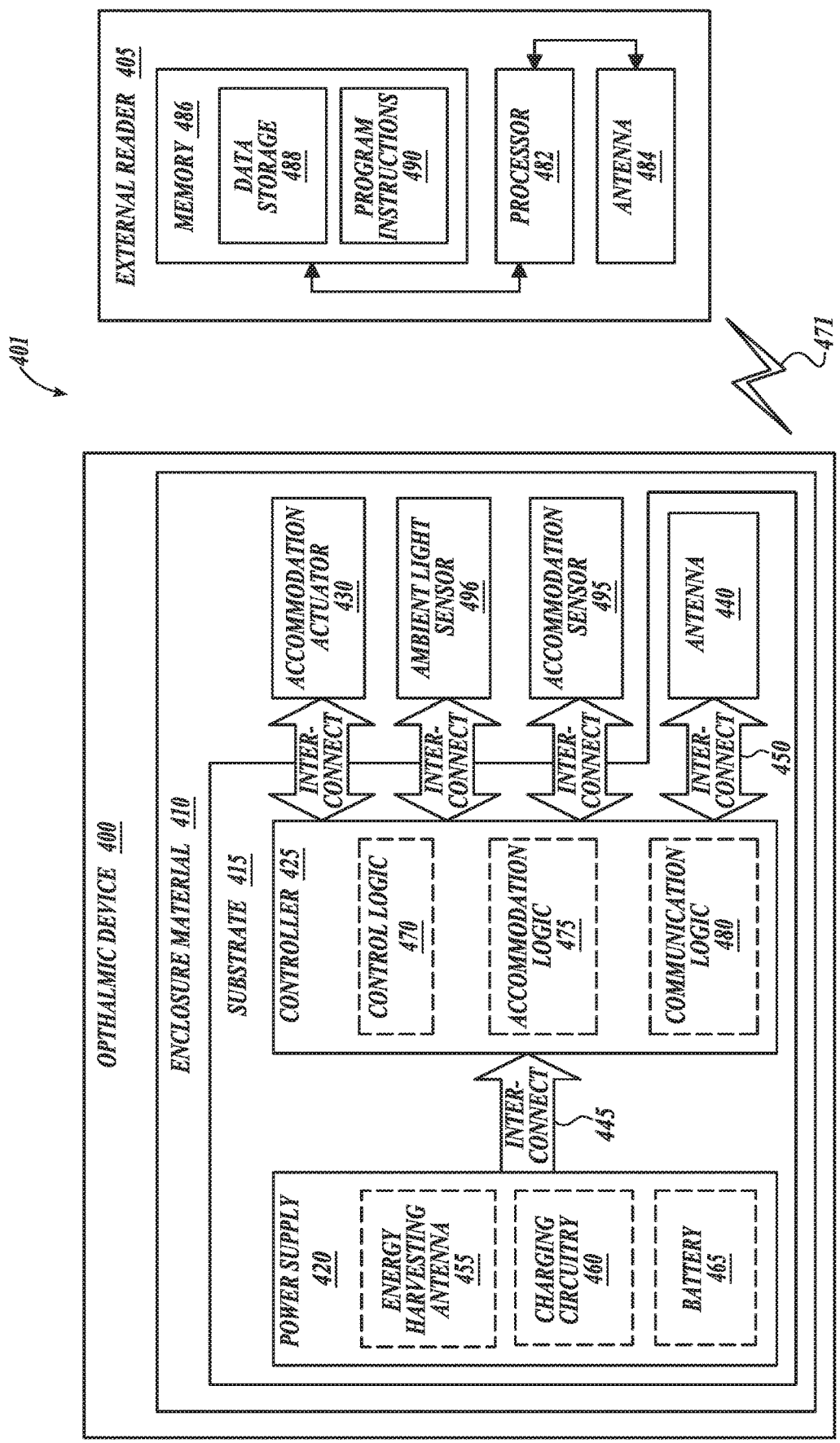
FIG. 4 is a schematic block diagram of another ophthalmic device, in accordance with an embodiment of the disclosure.

FIG. 4 is a functional block diagram of an ophthalmic device 400 including an ambient light sensor 496 and an accommodation sensor 495 in accordance with an embodiment of the present disclosure. In an embodiment, ophthalmic device 400 is an example of ophthalmic devices 100 and/or 200. Ophthalmic device 400 may be an on-eye device, such as a contact lens or a smart contact lens, or an implantable device, such as an intraocular lens. In the depicted embodiment, ophthalmic device 400 includes an enclosure material 410 formed to be either contact-mounted to a corneal surface of an eye or implanted into an eye. A substrate 415 is embedded within or surrounded by enclosure material 410 to provide a mounting surface for a power supply 420, a controller 425, an antenna 440, and various interconnects 445 and 450. The substrate 415 and the associated electronics may be one implementation of the controller 108. The illustrated embodiment of power supply 420 includes an energy harvesting antenna 455, charging circuitry 460, and a battery 465. The illustrated embodiment of controller 425 includes control logic 470, accommodation logic 475, and communication logic 480. As shown, accommodation actuator 430 is disposed in the enclosure material 410.

Power supply 420 supplies operating voltages to the controller 425 and/or the accommodation actuator 430. Antenna 440 is operated by the controller 425 to communicate information to and/or from ophthalmic device 400. In the illustrated embodiment, antenna 440, controller 425, and power supply 420 are disposed on/in substrate 415, while accommodation actuator 430 is disposed in enclosure material 410 (not in/on substrate 415). However, in other embodiments, the various pieces of circuitry and devices contained in ophthalmic device 400 may be disposed in/on substrate 415 or in enclosure material 410, depending on the specific design of ophthalmic device 400. For example, in one embodiment, accommodation actuator 430 may be disposed on a transparent substrate.

Substrate 415 includes one or more surfaces suitable for mounting controller 425, power supply 420, and antenna 440. Substrate 415 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 415 to form circuitry, electrodes, etc. For example, antenna 440 can be formed by depositing a pattern of gold or another conductive material on substrate 415. Similarly, interconnects 445 and 450 can be formed by depositing suitable patterns of conductive materials on substrate 415. A combination of resists, masks, and deposition techniques can be employed to pattern materials on substrate 415. Substrate 415 can be a relatively rigid material, such as polyethylene terephthalate ("PET") or another material sufficient to structurally support the circuitry and/or electronics within enclosure material 410. Ophthalmic device 400 can alternatively be arranged with a group of unconnected substrates rather than a single substrate 415. For example, controller 425 and power supply 420 can be mounted to one substrate 415, while antenna 440 is mounted to another substrate 415 and the two can be electrically connected via interconnects. Substrate 415 may also be a continuous piece of semiconductor, housing all or some of the aforementioned pieces of device architecture as integrated circuitry.

Substrate 415 can be shaped as a flattened ring with a radial width dimension sufficient to provide a mounting platform for the embedded electronic components. Substrate 415 can have a thickness sufficiently small to allow substrate 415 to be embedded in enclosure material 410 without adversely influencing the profile of ophthalmic device 400. Substrate 415 can have a thickness sufficiently large to provide structural stability suitable for supporting the electronics mounted thereon. For example, substrate 415 can be shaped as a ring with a diameter of about 10 millimeters, a radial width of about 1 millimeter (e.g., an outer radius 1 millimeter larger than an inner radius), and a thickness of about 50 micrometers. Substrate 415 can optionally be aligned with the curvature of the eye-mounting surface of ophthalmic device 400 (e.g., convex surface). For example, substrate 415 can be shaped along the surface of an imaginary cone between two circular segments that define an inner radius and an outer radius. In such an example, the surface of substrate 415 along the surface of the imaginary cone defines an inclined surface that is approximately aligned with the curvature of the eye mounting surface at that radius.

In the illustrated embodiment, power supply 420 includes a battery 465 to power the various embedded electronics, including controller 425. Battery 465 may be inductively charged by charging circuitry 460 and energy harvesting antenna 455. In one embodiment, antenna 440 and energy harvesting antenna 455 are independent antennae, which serve their respective functions of energy harvesting and communications. In another embodiment, energy harvesting antenna 455 and antenna 440 are the same physical antenna that are time shared for their respective functions of inductive charging and wireless communications with reader 405. Additionally or alternatively, power supply 420 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 460 may include a rectifier/regulator to condition the captured energy for charging battery 465 or directly power controller 425 without battery 465. Charging circuitry 460 may also include one or more energy storage devices to mitigate high frequency variations in energy harvesting antenna 455. For example, one or more energy storage devices (e.g., a capacitor, an inductor, etc.) can be connected to function as a low-pass filter.

Controller 425 contains logic to choreograph the operation of the other embedded components. Control logic 470 controls the general operation of ophthalmic device 400, including providing a logical user interface, power control functionality, etc. Accommodation logic 475 includes logic for receiving signals from sensors monitoring the orientation of the eye, determining the current gaze direction or focal distance of the user, such as accommodation sensor 495, from ambient light sensor 496, and manipulating accommodation actuator 430 (focal distance of the ophthalmic device 400) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 480 provides communication protocols for wireless communication with reader 405 via antenna 440. In one embodiment, communication logic 480 provides backscatter communication via antenna 440 when in the presence of an electromagnetic field 471 output from reader 405. In one embodiment, communication logic 480 operates as a smart wireless radio-frequency identification ("RFID") tag that modulates the impedance of antenna 440 for backscatter wireless communications. The various logic modules of controller 425 may be implemented in software/firmware executed on a general purpose microprocessor, in hardware (e.g., application specific integrated circuit), or a combination of both.

As discussed further herein with respect to FIGS. 1A-1C, control logic 470 may include logic for manipulating the measuring of the biological accommodation signals with accommodation sensor 495 based upon the ambient light signal generated by ambient light sensor 496. In this regard, measuring the biological accommodation signals may be tailored based upon the ambient light conditions to balance power consumption of the ophthalmic device 400 with accurate/precise generation of accommodation control signal based upon the measuring of the biological accommodation signals. As discussed further herein, the sensitivity of the eye to defocus is based in part on a level of ambient light. At lower ambient light levels, the eye is generally more susceptible to defocus and, accordingly, the accommodation actuator 430 may be driven based upon more accurate/ precise accommodation control signal to compensate for this increased susceptibility. Accordingly, manipulating the measuring of the biological accommodation signals may be based upon the ambient light signal.

Ophthalmic device 400 may include various other embedded electronics and logic modules. For example, a light source or pixel array may be included to provide visible feedback to the user. An accelerometer or gyroscope may be included to provide positional, rotational, directional or acceleration feedback information to controller 425.

The illustrated embodiment also includes reader 405 with a processor 482, an antenna 484, and memory 486. Memory 486 in reader 405 includes data storage 488 and program instructions 490. As shown reader 405 may be disposed outside of ophthalmic device 400, but may be placed in its proximity to charge ophthalmic device 400, send instructions to ophthalmic device 400, and/or extract data from ophthalmic device 400. In one embodiment, reader 405 may resemble a conventional contact lens holder that the user places ophthalmic device 400 in at night to charge, extract data, clean the lens, etc.

External reader 405 includes an antenna 484 (or group of more than one antennae) to send and receive wireless signals 471 to and from ophthalmic device 400. External reader 405 also includes a computing system with a processor 482 in communication with a memory 486. Memory 486 is a non-transitory computer-readable medium that can include, without limitation, magnetic disks, optical disks, organic memory, and/or any other volatile (e.g., RAM) or non-volatile (e.g., ROM) storage system readable by the processor 482. Memory 486 can include a data storage 488 to store indications of data, such as data logs (e.g., user logs), program settings (e.g., to adjust behavior of ophthalmic device 400 and/or external reader 405), etc. Memory 486 can also include program instructions 490 for execution by processor 482 to cause the external reader 405 to perform processes specified by the instructions 490. For example, program instructions 490 can cause external reader 405 to provide a user interface that allows for retrieving information communicated from ophthalmic device 400 or allows transmitting information to ophthalmic device 400 to program or otherwise select operational modes of ophthalmic device 400. External reader 405 can also include one or more hardware components for operating antenna 484 to send and receive wireless signals 471 to and from ophthalmic device 400.

External reader 405 can be a smart phone, digital assistant, or other portable computing device with wireless connectivity sufficient to provide the wireless communication link 471. External reader 405 can also be implemented as an antenna module that can be plugged into a portable computing device, such as in an embodiment where the communication link 471 operates at carrier frequencies not commonly employed in portable computing devices. In some instances, external reader 405 is a special-purpose device configured to be worn relatively near a wearer's eye to allow the wireless communication link 471 to operate with a low power budget. For example, the external reader 405 can be integrated in a piece of jewelry such as a necklace, earing, etc. or integrated in an article of clothing worn near the head, such as a hat, headband, etc.

Figure 3:
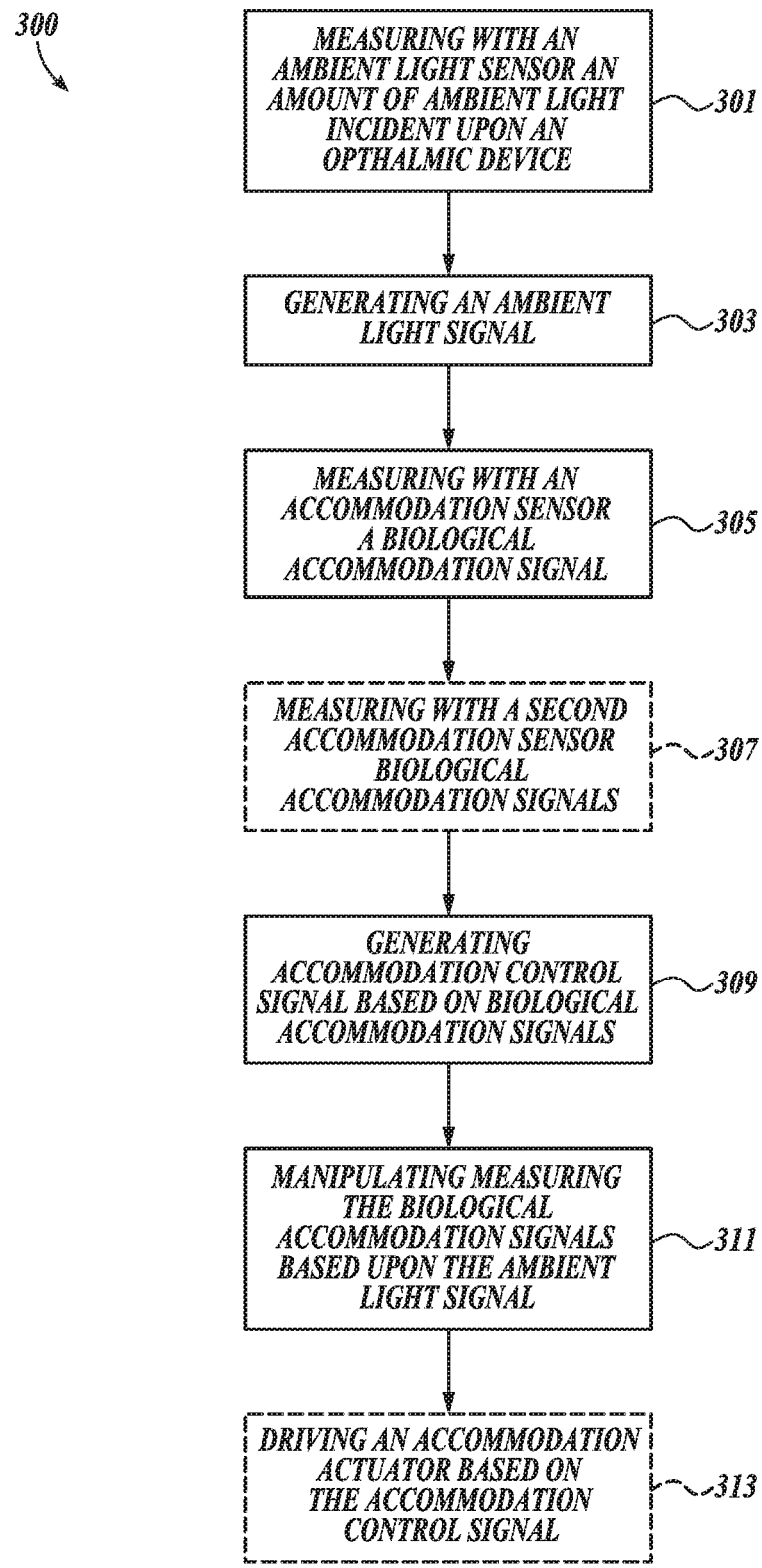
FIG. 3 is a block diagram of a method of operation of an ophthalmic device, in accordance with an embodiment of the disclosure.

FIG. 3 is a block diagram of a method 300 of operation of an ophthalmic device, in accordance with an embodiment of the disclosure. In an embodiment, the ophthalmic device is an example of ophthalmic devices 100, 200, and/or 400.

Method 300 may begin with process block 301, which includes measuring, with an ambient light sensor of the ophthalmic device, a brightness of ambient light incident upon the ophthalmic device mounted in or on an eye. Such measurement can include directly measuring light incident upon the ophthalmic device, such as with a light-sensitive-element disposed on the ophthalmic device, as discussed further herein with respect to FIGS. 2A-2D. Measuring of the ambient light can also include measuring a diameter of a pupil of the eye on or in which the ophthalmic device is mounted, as discussed further herein with respect to FIGS. 1A-1C. In an embodiment, measuring a brightness of ambient light is performed with a plurality of ambient light sensors, such as ambient light sensors 104A-104D of ophthalmic device 100, positioned to face a pupil of the eye, as described further herein with respect to FIGS. 1A-1C.

Process block 301 may be followed by process block 303, which includes generating an ambient light signal based upon the ambient light incident upon the ophthalmic device. In an embodiment, the ambient light signal is generated by the ambient light sensor. In an embodiment, the ambient light signal is based on a level or amount of ambient light incident upon the ophthalmic device.

Process block 303 may be followed by process block 305, which includes measuring biological accommodation signals with an accommodation sensor based on a target optical power of the eye. In an embodiment, the biological accommodation signals include a position and/or a displacement of ciliary muscles of the eye and measuring the biological accommodation signals includes measuring a position and/or a displacement of the ciliary muscles. As discussed further herein, the position and/or displacement of the ciliary muscles can be used to infer a target optical power of an eye. The sensor can include an ultrasound transducer configured to emit ultrasound and receive reflected/scattered ultrasound reflected and/or scattered off of the ciliary muscles. The sensor can include, for example, a light source configured to emit light and a light sensor positioned to receive reflected/scattered light.

In an embodiment, the biological accommodation signals include an electrical activity of ciliary muscles of the eye and measuring the biological accommodation signals includes measuring the electrical activity of the ciliary muscles. Such electrical activity of the ciliary muscles may be used to infer a target optical power of the eye. In an embodiment, the accommodation sensor is configured to measure electrical activity of the ciliary muscles is an electromyography sensor.

Process block 305 may be followed by process block 307, which includes measuring biological accommodation signals with a second accommodation sensor. In an embodiment, process block 307 is optional. In an embodiment, measuring with the second accommodation sensor occurs when a level or amount of the ambient light signal is below a predetermined level or amount. As discussed further herein, the eye is more susceptible to defocus in low-light conditions. Accordingly, the second accommodation sensor may be activated in order to compensate for this low-light susceptibility to defocus, particularly where the second accommodation sensor is more accurate and/or precise than the first accommodation sensor. In an embodiment, the second accommodation sensor has a higher power consumption rate than the first accommodation sensor. In this regard, the second accommodation sensor having a higher power consumption rate is activated under low-light conditions when additional accurate and/precise measurement of biological accommodation forces may be suitable to compensate for low-light susceptibility to defocus.

In an embodiment, the second accommodation sensor is a time-of-flight accommodation sensor. In an embodiment, measuring the biological accommodation signals with the second accommodation sensor includes measuring a time between emitting a time-of-flight interrogation signal and receiving reflected/scattered time-of-flight interrogation signal. Such time-of-flight accommodation sensors, while generally accurate in determining a target optical power of an eye, consume power at a relatively high rate compared to some other accommodation sensors. Accordingly, in an embodiment the second accommodation sensor, such as a time-of-flight accommodation sensor, is employed in low-light conditions to conserve power.

Process blocks 305 and/or 307 may be followed by process block 309, which includes manipulating the measuring of the biological accommodation signals based upon the ambient light signal. As discussed further herein, by manipulating the measuring of the biological accommodation signals based upon the ambient light signals, accommodation control signal based upon the biological accommodation signals can be tailored to a level of ambient light incident upon the ophthalmic device.

In an embodiment, manipulating the measuring of the biological accommodation signals includes manipulating a number of biological accommodation signal measurements, an averaging window of biological accommodation signal measurements, a biological accommodation signal measurement frequency, a biological accommodation signal sampling rate, and combinations thereof used to generate the accommodation controls signal.

Such manipulations can include manipulating the measuring of the biological accommodation signals to be more accurate and/or more precise, such as under low-light conditions, such as below a predetermined level, in which the eye is more susceptible to defocus. In that regard, in an embodiment, manipulating the measuring of the biological accommodation signals includes, for example, increasing a number of biological accommodation signal measurements, increasing a biological accommodation signal measurement frequency, increasing a biological accommodation signal sampling rate, and/or increasing a size of an averaging window of biological accommodation signal measurements.

In an embodiment, such manipulations include measuring biological accommodations signals in a manner configured to reduce power consumption, such as under bright-light conditions, such as at or above a predetermined level, in which the eye is less susceptible to defocus than in bright-light conditions. In that regard, manipulating the measuring of the biological accommodation signals includes, for example, decreasing a number of biological accommodation signal measurements, decreasing a biological accommodation signal measurement frequency, decreasing a biological accommodation signal sampling rate, and/or decreasing a size of an averaging window of biological accommodation signal measurements.

In an embodiment, manipulating the measuring of the biological accommodation signals includes increasing a gain of an amplifier, wherein the amplifier is operatively coupled to the accommodation sensor. In this regard, the biological accommodation signals may be amplified and accommodation control signal based on the amplified biological accommodation signals may be more accurate and/or precise than when unamplified. In an embodiment the biological accommodation signal amplified by the amplifier includes electrical activity of the ciliary muscles and the accommodation sensor includes an electromyography sensor configured to measure electrical activity of ciliary muscles of the eye.

Process block 309 may be followed by process block 311, which includes generating an accommodation control signal based upon the measuring of the biological accommodation signals. In an embodiment, the accommodation control signal is more accurately and/or more precisely based upon the biological control signals when the level of the ambient light signal is below the predetermined level. By manipulating the measuring of the biological accommodation signals to be more accurate and/or precise when below a predetermined level, the accommodation control signal may also be more closely based on the target optical power of the eye in order to compensate for the eye's natural susceptibility to defocus under low-light conditions.

Process block 311 may be followed by process block 313, which includes driving an accommodation actuator of the ophthalmic device, based at least in part on the accommodation control signal, to change an optical power of the ophthalmic device. In that regard, the method includes adjusting an optical power of the ophthalmic device based upon the biological accommodation signals, as measured. In an embodiment, process block 313 is optional. The accommodation actuator can include a liquid crystal configured to change an optical power of the ophthalmic device in response to accommodation control signal. The accommodation actuator can include an electro-wetting device configured to change an optical power of the ophthalmic device in response to accommodation control signal.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device shaped to be mounted on or in an eye, the ophthalmic device comprising:
    an ambient light sensor positioned to measure directly or indirectly ambient light incident upon the eye when the ophthalmic device is mounted on or in the eye;
    a first accommodation sensor configured to measure accommodation signals indicative of a target optical power of the eye;
    a second accommodation sensor configured to measure the accommodation signals of the eye and a generate second accommodation control signal based on the accommodation signals, wherein the second accommodation sensor has a power-consumption rate greater than a power-consumption rate of the first accommodation sensor;
    an accommodation actuator configured to change an optical power of the ophthalmic device; and
    a controller operatively coupled to the ambient light sensor, the second accommodation sensor, the accommodation actuator, and the first accommodation sensor, the controller including logic that, when executed by the controller, causes the ophthalmic device to perform operations including:
        measuring a brightness of the ambient light incident upon the eye with the ambient light sensor, wherein measuring a brightness of the ambient light incident upon the eye includes generating an ambient light signal based on the brightness of the ambient light incident upon the eye;
        measuring the accommodation signals with the first accommodation sensor;
        measuring the accommodation signals by activating the second accommodation sensor when a level of the ambient light signal is below a predetermined level;
        manipulating the measuring of the accommodation signals based upon the brightness of the ambient light;
        generating an accommodation control signal based upon the measuring of the accommodation signals as manipulated, wherein generating the accommodation control signal includes generating the accommodation control signal more accurately or more precisely based on the accommodation signal when the level of the ambient light signal is below the predetermined level than when the level of the ambient light signal is at or above the predetermined level; and
        driving the accommodation actuator based at least in part on the accommodation control signal to change an optical power of the ophthalmic device.

2. The ophthalmic device of claim 1, wherein an optical power of the eye on or in which the ophthalmic device is mounted and as adjusted by the accommodation actuator is closer to the target optical power when the level of the ambient light signal is below the predetermined level than when the level of the ambient light signal is at or above the predetermined level.

3. The ophthalmic device of claim 1, wherein manipulating the measuring of the accommodation signals includes at least one of manipulating a number of accommodation signal measurements, an averaging window of accommodation signal measurements, a accommodation signal measurement frequency, a accommodation signal sampling rate, and combinations thereof used to generate the accommodation controls signal.

4. The ophthalmic device of claim 1, wherein a power consumption rate of the ophthalmic device is higher when the level of the ambient light signal is below the predetermined level.

5. The ophthalmic device of claim 1, wherein the accommodation sensor includes an electromyography sensor configured to measure electrical activity of ciliary muscles of the eye,
    the ophthalmic device further comprising an amplifier configured to amplify a level of the accommodation control signal, wherein the controller further includes logic that, when executed by the controller, causes the ophthalmic device to perform operations including:
    increasing a gain of the amplifier when the level of the ambient light signal is below the predetermined level.

6. The ophthalmic device of claim 1, wherein the ambient light sensor is shaped and positioned to measure a diameter of a pupil when the ophthalmic device is mounted on or in the eye.

7. The ophthalmic device of claim 6, wherein the ambient light sensor is shaped to face a pupil of the eye when the ophthalmic device is mounted in or on the eye, and wherein the ambient light sensor is configured to generate the ambient light signal based on light reflected or scattered off of an iris of the eye.

8. The ophthalmic device of claim 1, wherein the ambient light sensor includes a light-sensitive element positioned face away from a body of a user when the ophthalmic device is mounted on or in the eye and to measure the light incident upon the ophthalmic device.

9. A method of operation of an ophthalmic device, the method comprising:
    directly or indirectly measuring a brightness of ambient light incident upon an eye on or in which the ophthalmic device is mounted with an ambient light sensor of the ophthalmic device;
    measuring accommodation signals indicative of a target optical power of the eye with a first accommodation sensor and activating a second accommodation sensor to measure the accommodation signal when the brightness of the ambient light is below a predetermined level, wherein the second accommodation sensor has a power-consumption rate that is greater than a power-consumption rate of the first accommodation sensor;
    generating an accommodation control signal based upon the measuring of the accommodation signals, wherein adjusting the optical power of the ophthalmic device includes driving an accommodation actuator of the ophthalmic device based at least in part on the accommodation control signal to change an optical power of the ophthalmic device, wherein generating the accommodation control signal includes generating the accommodation control signal more accurately or more precisely based on the accommodation signals when the brightness of the ambient light is below the predetermined level than when the brightness of the ambient light is at or above the predetermined level;
    manipulating the measuring of the accommodation signals based upon the brightness of the ambient light; and
    adjusting an optical power of the ophthalmic device based upon the accommodation signals, as manipulated.

10. The method of claim 9, wherein an optical power of the eye on or in which the ophthalmic device is mounted and as adjusted by the ophthalmic device is closer to the target optical power when the brightness of the ambient light is below the predetermined level than when the brightness of the ambient light is at or above the predetermined level.

11. The method of claim 9, wherein manipulating the measuring of the accommodation signals includes at least one of manipulating a number of accommodation signal measurements, an averaging window of accommodation signal measurements, a accommodation signal measurement frequency, a accommodation signal sampling rate, or combinations thereof used to generate the accommodation controls signal.

12. The method of claim 9, wherein a power consumption rate of the ophthalmic device is higher when the brightness of the ambient light is below the predetermined level.

* * * * *